United States Patent [19]

Andersson

[11] Patent Number: 5,068,272

[45] Date of Patent: Nov. 26, 1991

[54] NOVEL POLYSTYRENESULFONATE, USEFUL AGAINST CARDIAC ARRHYTHMIAS

[75] Inventor: Kjell H. Andersson, Fjärås, Sweden

[73] Assignee: Aktiebolaget Hassle, Molndal, Sweden

[21] Appl. No.: 539,863

[22] Filed: Jun. 18, 1990

[30] Foreign Application Priority Data

Jun. 29, 1989 [SE] Sweden .................................. 8902236

[51] Int. Cl.$^5$ ............................ C08K 5/41; C08J 3/00; C07C 255/50
[52] U.S. Cl. .................................... 524/155; 523/310; 558/413
[58] Field of Search ......................................... 524/155

[56] References Cited

PUBLICATIONS

Almgren et al., Chem. Abstracts, vol. 112, No. 1, 7180y (1990).
Copy of CAS Online Structural Search.

Primary Examiner—Johann Richter
Attorney, Agent, or Firm—White & Case

[57] ABSTRACT

A salt of 4-[3-[3-[ethyl-[3-(propylsulfinyl)propyl-]amino]-2-hydroxyproproxy]-benzonitrile having the formula I

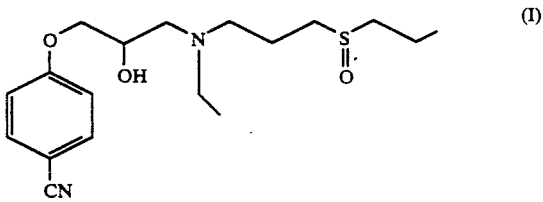

with polystyrenesulponic acid, which is useful for the treatment of cardiac arrhythmia, process for the preparation of said salt as well as the use of said salt for the preparation of medicaments with action against cardiac arrhythmias.

11 Claims, No Drawings

NOVEL POLYSTYRENESULFONATE, USEFUL AGAINST CARDIAC ARRHYTHMIAS

FIELD OF THE INVENTION

The invention relates to a novel polystyrenesulfonate, process for its preparation and its use.

More particularly, the present invention relates to the salt of the compound 4-[3-[ethyl[3-(propylsulfinyl)-propyl]amino]-2-hydroxypropoxy]-benzonitrile with polystyrenesulfonic acid, its preparation and use.

BACKGROUND OF THE INVENTION

Our prior patent application PCT/SE88/00691, filed on Dec. 20, 1988 and published after the filing date of this application, relates to a group of novel compounds which are useful in the treatment, acute as well as long term, of cardiac arrhythmias of diverse etiology. Among the compounds included in the group of compounds disclosed in said application is the compound 4-[3-[ethyl[3-(propylsulfinyl)propyl]amino]-2-hydroxypropoxy]-benzonitrile having the formula I

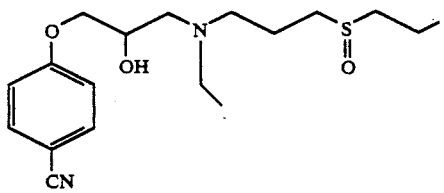

which can be obtained as a stereoisomeric mixture as well as in the form av the different stereoisomers, for instance:

4-[3-[ethyl[3-(propylsulfinyl)propyl]amino]-2(R)-hydroxypropoxy]-benzonitrile,

4-[3-[ethyl[3-(propylsulfinyl)propyl]amino]-2(S)-hydroxypropoxy]-benzonitrile.

The stereoisomeric mixture as well as the above mentioned pure stereoisomers can be obtained by oxidizing the appropriate 4-[3-[ethyl[3-(propylthio)-propyl]amino]-2-hydroxy]benzonitrile with m-chloroperbenzoic acid or analogous to methods disclosed in the above mentioned prior patent application.

The compound of the formula I in its base form is an oil.

THE INVENTION

It has now been found that the salt of the compound of formula I with polystyrenesulfonic acid is a valuable new product having the same basic antiarrhythmic effect as the compound of the formula I but being a solid.

Accordingly the present invention relates to the salt of the compound of the formula I with polystyrenesulfonic acid.

According to one embodiment of the salt according to the invention the compound of the formula I is present in the form of stereoisomeric mixture.

According to another embodiment of the present invention the compound of the formula I is present in the form of one of the pure stereoisomers.

Examples of stereoisomers are, in addition to the two stereoisomers mentioned above, the following:

4-[3-[ethyl[3-((R*)-propylsulfinyl)propyl]amino]-2(R)-hydroxypropoxy]-benzonitrile 4-[3-[ethyl[3-((S*)-propylsulfinyl)propyl]amino]-2(R)-hydroxypropoxy]-benzonitrile 4-[3-[ethyl[3-((R*)-propylsulfinyl)propyl]amino]-2(S)-hydroxypropoxy]-benzonitrile, and 4-[3-[ethyl[3-((S*)-propylsulfinyl)propyl]amino]-2(S)-hydroxypropoxy]-benzonitrile The present invention also relates to a process for the preparation of the salt according to the present invention, which process comprises reacting the compound of the formula I above with polystyrenesulfonic acid.

Polystyrenesulfonic acid is preferably used in the form of small particles.

Usually the polystyrenesulfonic acid is cross-linked with divinylbenzene, the degree of crosslinking preferably being 2–10%.

According to one embodiment of the process according to the invention small particles of polystyrenesulfonic acid, either in the acid ($H^+$) form or in the form of a salt with a metal ion suited for ion exchange reactions, e.g. $Na^+$, $K^+$ or $Ca^{2+}$, are added to a solution of the compound having the formula I and of a suitable salt of said compound, respectively, in a suitable reaction medium.

According to another embodiment of the process according to the invention small particles of polystyrenesulfonic acid in the form of a salt with a metal ion suited for ion exchange reactions are packed into a column for ion exchange operations and a solution of the compound having the formula I in the form of a suitable salt is applied to the column.

The invention further relates to a method of preventing or reducing cardiac arrhythmias in mammals, including man, which comprises administering to a host in need of such treatment an effective amount of the salt of the compound of the formula I with polystyrenesulfonic acid.

The invention yet further relates to the salt of the compound of the formula I with polystyrenesulfonic acid for use as a medicament, particularly as an antiarrhythmic agent.

The invention also relates to the use of the salt of the compound of the formula I with polystyrenesulfonic acid for the manufacture of medicaments with action against cardiac arrhythmias.

The following non-limiting examples further illustrate the invention.

EXAMPLE 1

The polystyrenesulfonate of 4-[3-[ethyl[3-(propylsulfinyl)-propyl]amino]-2-hydroxypropoxy]-benzonitrile To a stirred solution of 4-[3-[ethyl[3-(propylsulfinyl)-propyl]-amino]-2-hydroxypropoxy]-benxonitrile (92.28 g) in methanol (900 ml) was added polystyrenesulfonic acid (63.15 g) at 0° C. under nitrogen atmosphere. Stirring was continued for 18 h. The resin was filtered, washed with methanol (500 ml), extracted in a Soxhlet extractor at room temperature over night with ethanol and finally dried under high vacuum to constant weight. Analysis showed 59.3% binding of active substance.

EXAMPLE 2

The polystyrenesulfonate of 4-[3-[ethyl[3-(propylsulfinyl)-propyl]amino]-2-hydroxypropoxy]-benzonitrile To a stirred solution of 4-[3-[ethyl[3-(propylsulfinyl)-propyl]amino]-2-hydroxypropoxy]-benzonitrile × HCl (5.5 g) in ethanol:water (1:1) (30 ml) was added sodium polystyrenesulfonate (5 g) at room temperature. After 30 minutes the resin was filtered and washed with ethanol:water (1:1) three times, dried under high vacuum to constant weight.

Analysis showed 32% binding of active substance.

EXAMPLE 3

4-[3-[ethyl[3-(propylsulfinyl)propyl]amino]-2-hydroxypropoxy]-benzonitrile 2.45 g of 4-[3-[ethyl[3-(propylthio)propyl]amino]-2-hydroxypropoxy]-benzonitrile and 1.4 g p-toluenesulfonic acid were mixed in 50 ml of ethanol. The mixture was cooled to −10° C. and 1.7 g of m-chloroperbenzoic acid was added in small protions. The mixture was stirred for 0.5 hour at −10° C. and one hour at room temperature and then evaporated. The residue was dissolved in dichloromethane and washed with three portions of sodium carbonate and twice with water and thereafter dried over sodium sulfate, filtrated and evaporated. The residue, 2.3 g yellow oil, was purified by column chromatography. Yield: 1.4 g of the title compound.

NMR: $^{13}$C in CDCl$_3$; 11.21, 11.33, 13.11, 16.02, 20.30, 20.43, 47.41, 47.45, 49.69, 49.95, 52.18, 52.41, 54.29, 54.41, 56.06, 56.09, 66.08, 70.41, 70.49, 103.76, 115.09, 118.83, 133.62, 161.88 ppm

EXAMPLE 4

4-[3-[ethyl[3-(propylsulfinyl)propyl]amino]-2(R)-hydroxypropoxy]-benzonitrile Oxidation of 4-[3-[ethyl[3-(propylthio)propyl]amino]-2(R)-hydroxypropoxy]benzonitrile with m-chloroperbenzoic acid was carried out as described for the stereoisomeric mixture in example 3. $[\alpha]_D^{20}$ −18.6° (C 1.0, CH$_3$OH).

NMR: $^{13}$C in CDCl$_3$; 11.35, 11.47, 13.30, 16.24, 20.47, 20.62, 47.59, 47.63, 49.83, 50.12, 52.30, 52.57, 54.53, 54.66, 56.28, 56.31, 66.13, 70.52, 70.60, 104.08, 115.24, 119.02, 133.85, 162.0 ppm.

EXAMPLE 5

4-[3-[ethyl[3-(propylsulfinyl)propyl]amino]-2(S)-hydroxypropoxy]-benzonitrile The title compound was prepared in analogy with method described in example 4 and example 3. $[\alpha]_D^{20}$ +18.0° (C 1.0, CH$_3$OH).

NMR: $^{13}$C in CDCl$_3$; 11.31, 11.43, 13.26, 16.18, 20.41, 20.57, 47.53, 47.58, 49.8, 50.08, 52.26, 52.53, 54.48, 54.61, 56.22, 56.24, 66.09, 70.48, 70.57, 104.0, 115.20, 118.97, 133.79, 161.96 ppm.

Any of the isomers prepared according to Examples 4 and 5 may replace the stereoisomeric mixture used in Examples 1 and 2.

EXAMPLE 6

4-[3-[ethyl[3-((S*)-propylsulfinyl)propyl]amino]-2(R)-hydroxypropoxy]-benzonitrile a) Ethyl (3-(S*)-propylsulfinyl)propylamine

A hot solution of 27.2 g (0.1 mol) of (−)-1,3,2-dioxaphosphorinane-5,5-dimethyl-2-hydroxy-4-(2-methoxyphenyl)-2-oxide and 17.73 g (0.1 mol) of racemic ethyl (3-propylsulfinyl)-propylamine in 750 ml of acetone and 32.5 ml of methanol was allowed to cool to room temperature, yielding 23.9 g of crystalline material. The experiment was repeated on a 0.25 mol scale, this time yielding 53.0 g of crystals. The combined crops were recrystallized five times from acetone-methanol finally yielding 8.95 g of salt.

A solution of 15.06 g (0.0392 mol) of trioctylamine in dichloromethane was shaken with 19.6 ml of 2M hydrochloric acid. The phases were separated and the organic layer was washed with water. The organic phase, now containing trioctylammonium chloride, was stirred for 90 min. with a solution of 8.8 g (0.0196 mol) of the above mentioned resolved salt in water. The phases were separated, and the organic layer was washed with water. The combined aqueous phases were washed with dichloromethane, and then brought to pH 11.5 with 10M sodium hydroxide. Extraction four times with dichloromethane yielded 2.3 g of laevorotatory amine base, arbitrarily denoted S* $[\alpha]_D^{20}$ −8.0° (c=1, CH$_3$OH).

$^{13}$C NMR (as salt with (−)-1,3,2-dioxaphosphorinane-5,5-dimethyl-2-hydroxy-4-(2-methoxyphenyl)-2-oxide); in CDCl$_3$: 10.80, 12.95, 15.81, 17.55, 19.49, 19.58, 20.41, 36.59, 36.61, 42.37, 45.50, 48.73, 53.67, 54.71, 76.79, 76.83, 77.34, 109.63, 119.69, 126.42, 126.50, 128.33, 128.93, 155.83.

b) (R)-4-(oxiranylmethoxy)-benzonitrile

A solution of 2.71 g of (2S)-1-(4-cyanophenoxy)-3-methane-sulfonyloxypropan-2-ol in 40 ml of 1,2-dimethoxyethane was stirred with 1.0 g of powdered sodium hydroxide at room temperature for 22 h. 10 ml of saturated sodium chloride solution was added, and the mixture was extracted twice with ether. Washing with 5% sodium hydrogen carbonate, drying over magnesium sulfate, filtration and evaporation gave 1.76 g of crystalline material, m.p. 67.5° C., $[\alpha]_D^{20}$ −14.7° (c=1, acetone).

NMR: $^{13}$C in CDCl$_3$; 44.40, 49.71, 69.02, 104.59, 115.34, 118.95, 133.98, 161.66 ppm.

c) 4-[3-[ethyl[3-((S*)-propylsulfinyl)propyl]amino]-2(R)-hydroxypropoxy]-benzonitrile A mixture of 3 g of ethyl (3-(S*)-propylsulfinyl)-propylamine and 3.18 g of (R)-4-(oxiranylmethoxy)-benzonitrile was refluxed for 16 h in 25 ml of isopropyl alcohol. After evaporation of the solvent, the crude product was dissolved in 2M hydrochloric acid, washed with ether, the solution brought to pH 11.5 with 2M sodium hydroxide and extracted with dichloromethane. Evaporation of the organic phase gave 6.11 g of an oil, $^{13}$C NMR in CDCl$_3$: 11.23, 13.17, 16.08, 20.46, 47.41, 49.98, 52.41, 54.46, 56.11, 66.05, 70.50, 103.80, 115.13, 118.92, 133.69, 161.92 ppm.

EXAMPLE 7

4-[3-[ethyl[3-((R*)-propylsulfinyl)propyl]amino]-2(S)-hydroxypropoxy]-benzonitrile a) Ethyl (3-(R*)-propylsulfinyl)propylamine

Resolution of racemic ethyl (3-propylsulfinyl)-propylamine with (+)-1,3,2-dioxaphosphorinane-5,5-dimethyl-2-hydroxy-4-(2-methoxyphenyl)-2-oxide in analogy with example 1a gave dextrorotatory amine base. This compound, arbitrarily denoted R*, has the following data: $[\alpha]_D^{20}+7.6°$ (c=1, CH$_3$OH).

$^{13}$C NMR (as salt with (+)-1,3,2-dioxaphosphorinane-5,5-dimethyl-2-hydroxy-4-(2-methoxyphenyl)-2-oxide); in CDCl$_3$: 10.92, 13.07, 15.93, 17.66, 19.56, 19.70, 20.52, 36.72, 36.73, 42.48, 45.61, 48.85, 53.79, 54.82, 76.92, 76.96, 77.45, 77.49, 109.73, 119.81, 126.54, 126.62, 128.44, 129.06, 155.95.

b) (S)-4-(oxiranylmethoxy)-benzonitrile

From 2.7 g (2R)-1-(4-cyanophenoxy)-3-methanesulfonyloxypropan-2-ol in analogy with example 1b was obtained 1.75 g crystalline material; m.p. 68.0° C. $[\alpha]_D^{20}+14.5°$ (c=1, acetone).

$^{13}$C NMR in CDCl$_3$: 44.21, 49.58, 68.90, 104.25, 115.20, 118.86, 133.80, 161.53.

c)
4-[3-[ethyl[3-((R*)-propylsulfinyl)propyl]amino]-2(S)-hydroxypropoxy]-benzonitrile A mixture of 2.3 g of ethyl[(R*)-3-propylsulfinyl]-propylamine and 3.18 g of (S)-4-(oxiranylmethoxy)-benzonitrile in 19 ml of isopropyl alcohol was refluxed 16 h and thereafter worked up in analogy with 1c yielding 4.1 g of an oil; $[\alpha]_D^{20}+26.5°$ (c=1, CH$_3$OH).

$^{13}$C NMR in CDCl$_3$: 11.16, 13.05, 15.96, 20.37, 47.38, 49.87, 52.37, 54.31, 56.05, 66.10, 70.47, 103.65, 115.06, 118.78, 133.55, 161.86.

EXAMPLE 8

4-[3-[ethyl[3-((R*)-propylsulfinyl)propyl]amino]-2(R)-hydroxypropoxy]-benzonitrile A mixture of 2.3 g of ethyl[(R*)-3-propylsulfinyl]-propylamine and 2.5 g of (R)-4-(oxiranylmethoxy)-benzonitrile was refluxed for 16 h in 19 ml of isopropyl alcohol in analogy with example 1c. Traditional work up procedures gave 4.27 g of an oil; $[\alpha]_D^{20}-13.4°$ (c=1, CH$_3$OH).

$^{13}$C NMR in CDCl$_3$: 11.58, 13.36, 16.29, 20.57, 47.70, 49.96, 52.41, 54.64, 56.36, 66.24, 70.63, 104.18, 115.33, 119.07, 133.91, 162.09.

EXAMPLE 9

4-[3-[ethyl[3-((S*)-propylsulfinyl)propyl]amino]-2(S)-hydroxypropoxy]-benzonitrile A mixture of 2.3 g of ethyl(3-(S*)-propylsulfinyl)-propylamine and 2.5 g of (S)-4-(oxiranylmethoxy)-benzonitrile in 19 ml of isopropyl alcohol was refluxed for 24 h in analogy with example 1c. Traditional work up procedures gave 3.65 g of an oil; $[\alpha]_D^{20}+11.1°$ (c=1, CH$_3$OH).

$^{13}$C NMR in CDCl$_3$: 11.56, 13.33, 16.25, 20.54, 47.71, 49.92, 52.42, 54.53, 56.31, 66.33, 70.64, 104.03, 115.33, 119.06, 133.86, 162.11.

We claim:

1. The salt of the compound 4-[3-[ethyl[3-(propylsulfinyl)propyl]amino]-2-hydroxypropoxy]-benzonitrile having the formula I

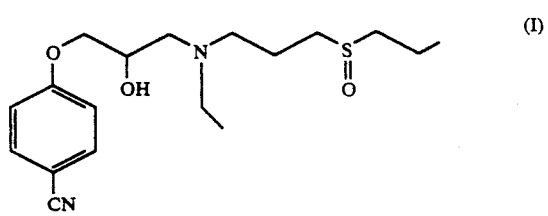

with polystyrenesulfonic acid, said compound being in the form of the stereoisomeric mixture or in the form of a pure stereoisomer thereof.

2. The salt according to claim 1, wherein the compound of the formula I is in the form of the stereoisomeric mixture.

3. The salt according to claim 1, wherein the compound of the formula I is in the form of one of the pure stereoisomers:
4-[3-[ethyl[3-(propylsulfinyl)propyl]amino]-2(R)-hydroxypropoxy]-benzonitrile,
4-[3-[ethyl[3-(propylsulfinyl)propyl]amino]-2(S)-hydroxypropoxy]-benzonitrile,
4-[3-[ethyl[3-((R*)-propylsulfinyl)propyl]amino]-2(R)-hydroxypropoxy]-benzonitrile,
4-[3-[ethyl[3-((S*)-propylsulfinyl)propyl]amino]-2(R)-hydroxypropoxy]-benzonitrile,
4-[3-[ethyl[3-((R*)-propylsulfinyl)propyl]amino]-2(S)-hydroxypropoxy]-benzonitrile, and
4-[3-[ethyl[3-((S*)-propylsulfinyl)propyl]amino]-2(S)-hydroxypropoxy]-benzonitrile.

4. A method for preventing or reducing cardiac arrhythmias in mammals which comprises administering to a host in need of such treatment an administering to a host in need of such treatment an effective amount of the salt of the compound 4-[3-[ethyl[3-(propylsulfinyl)propyl]amino]-2-hydroxypropoxy]-benzonitrile having the formula I

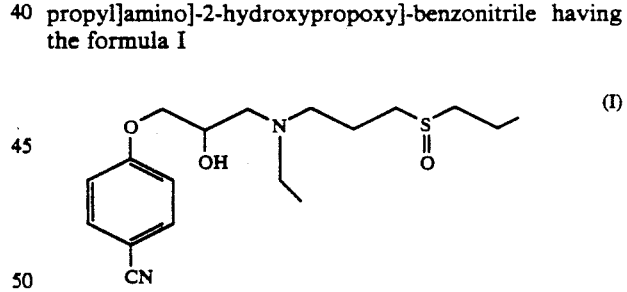

with polystyrenesulfonic acid, said compound being in the form of the stereoisomeric mixture or in the form of a pure stereoisomer thereof.

5. A method according to claim 4 wherein the salt is of the stereoisomeric mixture of the compound of formula I.

6. A method according to claim 4 wherein the salt is of the pure stereoisomer 4-[3-[ethyl[3-(propylsulfinyl)propyl]amino]-2(R)-hydroxy-propoxy]-benzonitrile.

7. A method according to claim 4 wherein the salt is of the pure stereoisomer 4-[3-[ethyl[3-(propylsulfinyl)propyl]amino]-2(S)-hydroxy-propoxy]-benzonitrile.

8. A method according to claim 4 wherein the salt is of the pure stereoisomer 4-[3-[ethyl[3-((R*)-propylsulfinyl)propyl]amino]-2(R)-hydroxypropyl]-benzonitrile.

9. A method according to claim 4 wherein the salt is of the pure stereoisomer 4-[3-[ethyl[3-((S*)-propylsulfinyl)propyl]amino]-2(R)-hydroxypropoxy]-benzonitrile.

10. A method according to claim 4 wherein the salt is of the pure stereoisomer 4-[3-[ethyl[3-((R*)-propylsulfinyl)propyl]amino]-2(S)-hydroxypropoxy]-benzonitrile.

11. A method according to claim 4 wherein the salt is of the pure stereoisomer 4-[3-[ethyl[3-((S*)-propylsulfinyl)propyl]amino]-2(S)-hydroxypropoxy]-benzonitrile.

* * * * *